United States Patent
Red'ko et al.

(10) Patent No.: US 7,071,684 B2
(45) Date of Patent: Jul. 4, 2006

(54) METHOD OF NON-CONTACT MEASURING ELECTRICAL CONDUCTIVITY OF ELECTROLYTES WITH USING PRIMARY MEASURING TRANSFORMER

(76) Inventors: Volodymyr Red'ko, 4956 Rothschild Dr., Coral Springs, FL (US) 33067; Volodymyr Khandetskyy, 30/125 Chicherina St., Dnipropetrovsk (UA) 49006; Elena Shembel, 4956 Rothschild Dr., Coral Springs, FL (US) 33067; Peter Novak, 2110 N. Ocean Blvd., Apt. 8A, Fort Lauderdale, FL (US) 33305

( * ) Notice: Subject to any disclaimer, the term of this patent is extended or adjusted under 35 U.S.C. 154(b) by 83 days.

(21) Appl. No.: 10/898,446

(22) Filed: Jul. 23, 2004

(65) Prior Publication Data

US 2005/0156604 A1     Jul. 21, 2005

(51) Int. Cl.
*G01R 27/00* (2006.01)
*G01R 33/20* (2006.01)
*G01R 33/30* (2006.01)
*G01N 27/72* (2006.01)
*G01N 27/00* (2006.01)

(52) U.S. Cl. ...................... 324/228; 324/691
(58) Field of Classification Search ............... 324/228, 324/691
See application file for complete search history.

(56) References Cited

U.S. PATENT DOCUMENTS

| | | | |
|---|---|---|---|
| 2,542,057 | A | 2/1951 | Relis |
| 4,220,920 | A | 9/1980 | Gross |
| 4,408,202 | A | 10/1983 | Fales |
| 4,820,990 | A | 4/1989 | Moore |
| 4,825,168 | A | 4/1989 | Ogava et al. |
| 5,077,525 | A | 12/1991 | West et al. |
| 5,157,332 | A | 10/1992 | Reese |

FOREIGN PATENT DOCUMENTS

FR        2782802 A1    3/2000

*Primary Examiner*—Bot LeDynh
(74) *Attorney, Agent, or Firm*—Howard & Howard (57) ABSTRACT

A method of noncontact measuring the electrical conductivity of electrolytes using a primary measuring transformer includes placing the electrolyte in a sampler, exciting an alternating magnetic field using an axisymmetrical eddy current sensor, switching to the sensor a capacitor of variable capacitance, tuning of the formed circuit in resonance with the frequency of the generator of harmonic oscillations, and recording the change in the introduced active resistance of the parametric eddy current sensor rated against its own inductive resistance.

19 Claims, 3 Drawing Sheets

METHOD OF NON-CONTACT MEASURING ELECTRICAL CONDUCTIVITY OF ELECTROLYTES WITH USING PRIMARY MEASURING TRANSFORMER

CROSS-REFERENCE TO RELATED APPLICATIONS

This application claims the benefit of Ukraine Patent Application No. 2003007005, filed Jul. 25, 2003; and Ukraine Patent No. 60954A, filed Oct. 15, 2003, which are incorporated herein by reference.

STATEMENT REGARDING FEDERALLY SPONSORED RESEARCH OR DEVELOPMENT

Not applicable.

FIELD OF THE INVENTION

The invention relates to electrical engineering industry, in particular to the field of measuring electrical properties of electrolytes used in chemical power sources, and refers to a method and a primary measuring transducer for measuring their electrical conductivity.

BACKGROUND OF THE INVENTION

The electrical conductivity of electrolytes in the majority of cases has been traditionally measured using a contact method. In such case the trustworthiness of the obtained results is greatly influenced by the contact phenomena. Let us discuss it on the basis of an example.

Let us assume that two identical metallic electrodes, for example, two platinum plates are immersed into a water solution of a copper vitriol. Let us pass current through the copper vitriol solution with the platinum electrodes by connecting the latter to an outer e.m.f. source. Then copper will be deposited on the platinum electrode that serves as a cathode while oxygen will be formed on the anode. This will result in a disturbance of the electrodes symmetry: one of them will be coated with a copper layer while the other will have a film of oxygen. This is also accompanied by a change in the electrolyte concentration at the electrodes: the salt concentration at the cathode decreases while an acid is formed at the anode. Now the electrodes immersed in the solution will not be identical, forming a galvanic element with its own e.m.f. E', the so called polarization element [1].

A similar disturbance of the initial symmetry that exists when the electrodes are of an identical material, will occur each time during the electrolysis of solutions. The change of the electrodes that occurs in such case is termed as polarization of electrodes, while the generated e.m.f. is termed as polarization e.m.f. Such polarization is not always reversible: after the discharge of the element the initial state may not be restored.

The generation of the polarization e.m.f. creates a number of serious problems.

In order to be deposited on the electrode the ions have to overcome a certain potential barrier. Work $A'=E'It$ is spent to overcome this barrier. The work spent for the emission of the Lenz-Joulean heat $Q=I^2Rt$ can be reduced; to this end it is necessary to change resistance R by using large electrodes to be arranged closely to one another. But work A' is unavoidable, and its value is a function of the electrolyte composition and the material of the electrodes. Value E' equals polarization e.m.f. only in cases when polarization of the electrodes is reversible. But in the majority of cases it is higher. In order to have the process of ions deposition on the electrode started, "overvoltage" is required which may equal several tenths of a Volt. Thus, in case of a reversible polarization of electrodes to start electrolysis of a sulfuric acid water solution, a 1.22 V difference of potentials would be required on the electrodes; but actually, when pure platinum electrodes are used, the electrolysis (that in this case leads to water decomposition) starts only at 1.64 V.

To weaken the influence of the electrochemical reactions on the electrolyte resistance being measured, the conductivity is measured using alternating current. This method is well known. The companies that produce liquid electrolytes indicate in their certificates the conductivity values measured at the alternating current, with the characteristics of the electrodes that are in contact with the electrolyte.

Among the disadvantages of the method for electrolyte conductivity measuring by using contact electrodes and the alternating current is the following. Depending on the nature of the solution and the mechanism of its ion conductivity in the general case for each solution there exists its own range of the alternating current frequency within which the conductivity does not depend on frequency. Therefore for each case it is necessary to determine this frequency range and the acceptable value of the alternating current voltage that is applied to the electrodes. Nevertheless this condition is not enough to guarantee the measurement reliability. The next important condition is the stability of the conductivity value being measured during a lengthy period. That will guarantee that on the electrodes within the given frequency range and given voltage there will be no reactions that may change the condition of the system.

The errors inherent to the contact methods of measuring the electric properties of electrolytes can be avoided by using noncontact eddy-current methods of measuring.

Known in the art are devices for measuring electrical conductivity of electrolytes using an eddy-current method.

According to U.S. Pat. No. 2,542,057, Relis, "Method and apparatus for measuring the conductivity of an electrolyte", Feb. 20, 1951, the conductivity of a liquid electrolyte is determined by immersing therein insulated primary and secondary inductance coil of toroidal shape. The primary coil is excited by the alternating current, the field of this coil induces eddy current in the electrolyte. The eddy current field is fixed by the secondary col. The eddy current value is a function of the specific electrical conductance of the liquid electrolyte. A thin copper screen is used which is arranged above the coils. To reduce the voltage level not related to the signal, an external compensating circuit is used.

According to U.S. Pat. No. 3,806,798, Gross, "Electrodless conductivity measuring system", Apr. 23, 1974, for measuring the conductivity of a liquid electrolyte an exciting and a measuring induction coils are also used According to this patent the interferences are compensated and the sensitivity of measurements are increased through relative arrangement of the coils, screening, introduction of an additional winding.

In U.S. Pat. No. 4,220,920, Gross, "Electrodless conductivity measuring system", Sep. 2, 1980, the exciting and the measuring coils immersed into a conducting liquid whose electrical conductivity is measured according to the voltage induced by the eddy current in the liquid on the measuring coil, are arranged in a certain manner relative ot each other. According to this patent the metrological characteristics are upgraded due to the special shape of the screens of the coils, arrangement of the windings and the signal processing circuit.

The advantageous feature of these patents is the noncontact measurements of the electrical conductivity of liquid electrolytes.

A common disadvantage of these patents is that the measurements are performed at one fixed frequency, without considering the issues related to the frequency dispersion of the specific electrical conductance of liquid electrolytes.

In the patent U.S. Pat. No. 4,408,202, Fales, "Electrokinetic display system", Oct. 4, 1983, is proposed a system for studying the electrical kinetics of solutions of liquid electrolytes with different concentrations. The electrolyte contains the reagents that take part in the reverse reaction during the electrolysis process. The reagents are self-induced or contain an indicator. Electric current is passed between the electrodes immersed into the liquid. To the electrolyte volume a variable magnetic field is applied, eddy currents are excited in the electrolyte while the magnetic field is spatially shifted. In such way the processes in the area of the electrodes are studied that are related to the movement and accumulation of the charge carriers in the electrolyte.

In the patent U.S. Pat. No. 4,820,990, Moore, "Electrodless detector", Apr. 11, 1989, it is proposed to use an inductive primary transducer placed on the sampler in the form of a dielectric cylinder, for studying the position of the spatial charge (ion cloud) in the near-electrode area of the electric double layer in heterogeneous electrochemical liquids. The inductive transducer is excited at a fixed frequency. An electric circuit with a signal processor is used to process the signal depending on the conditions of forming a spatial charge in the liquid electrolyte.

An advantage of these patents is that the use of a vortex magnetic field allows sounding the position and movement of the charge carriers in the near-electrode areas without immersing into these electrolyte areas of additional contact electrodes that would cause changes in the position of the charges.

A disadvantage is that the proposed solutions do not allow determining the frequency characteristics of the process of charges transfer in the electrolyte.

In the patent U.S. Pat. No. 4,825,168, Ogava et al, "Remote conductivity sensor using square wave excitation", Apr. 25, 1989, it is proposed to use an eddy current sensor in the form of an exciting and a pickup coils for on-line measuring the conductivity of a liquid. It is used to control the water quality in a water supply system. The sensor circuit includes an alternating current generator, digital timer, trigger, current-to-voltage converter, alternating current amplifier, synchronous detector.

An advantage of this patent is the noncontact measurement, its high sensitivity due to the use high frequencies of the field.

But when measuring the sensitivity of electrolytic media it is also necessary to take into regard the processes of periodic transfer (or spatial shift) of the linked charges under the influence of the alternating field that is not carried out according to this patent.

In the patent U.S. Pat. No. 5,157,332, Reese et al, "Three-toroid electrodeless conductivity cell", Oct. 20, 1992, it is proposed to use a three-coil system that is immersed into a liquid for measuring its electrical conductivity. The measurement is carried out in the stream of liquid. Two sensor configurations are used: in the first the two edge toroid coils are exciting while the middle one is pickup; in the second the middle coil is exciting while the two edge coils are pickup. The results obtained with the three-coil and two-coil systems are compared.

An advantage of this patent is the possibility of determining inhomogeneities within the volume of a liquid stream.

A disadvantage of the patent is the impossibility of studying conductivity within the frequency range.

In the patent FR 2782802 A1, Coudray et al, Mar. 03, 2000, parallel to the eddy current sensor a capacitor is switched in whose capacity can be varied. The parallel oscillatory circuit thus formed is switched to the generator of harmonic oscillations and the circuit is tuned in resonance with the generator frequency. The patent proposes using an oscillating circuit with a measuring circuit for measuring the specific electric resistance of an electroconducting liquid.

The use of a parallel resonant circuit offers advantages in the range of high frequencies (metric waves band) thus allowing to study high-resistance electrolytes.

But in the proposed circuit only one parameter of the eddy-current sensor can be measured: either the change of its active resistance or the change of its inductance at one frequency of the sounding field. There is no possibility for measurements within the frequency range.

The closest in its technical essence to the proposed invention is the method of noncontact measuring of the electrical conductivity of a liquid disclosed in the U.S. Pat. No. 5,077,525, West et al, "Electrodless conductivity sensor with inflatable surface", Dec. 31, 1991. In the patent it is proposed to generate and excite an alternating magnetic field by means of an unductance coil of toroidal shape, to measure the eddy current field induced by the field of the exciting coil in the liquid using a pickup coil of the same shape. The voltage introduced into the pickup coil is a function of the eddy current intensity in the liquid that is determined at the fixed intensity value of the exciting magnetic field according to the conductivity of the liquid. The outer surface of the converter is separated from the liquid with a flexible non-conducting 2–3 mm thick membrane. The patent includes means that effect vibration of the membrane thus cleaning it off the deposit that is electroconductive. Such a deposit introduces a serious error into the results of measuring the electrical conductivity of a liquid electrolyte.

The main advantages of this patent noncontact measuring and means for self-cleaning of the membrane surface that separates the operating end face of the sensor from the liquid.

The disadvantages of this method are absence of means for measuring the frequency dependence of the electrolyte conductivity, and also the fact that the flexible membrane forms an intricate surface configuration of the liquid relative to the pickup inductance coil of the sensor. In view of this only an approximate evaluation of the specific electrical conductance of the liquid electrolyte is possible. This method can be effectively used only for comparing the relative electrical conductivity values of liquids having approximately equal density.

SUMMARY

The main purpose of the invention is to obtain trustworthy results of measuring specific electrical conductivity of electrolytes.

This task is solved by means of a method of noncontact measuring the electrical conductivity of electrolytes using a primary measuring transducer that includes: placing an electrolyte in the sampler, exciting an alternating magnetic field using an axially symmetrical eddy current sensor, switching to the sensor a capacitor of variable capacitance, tuning of the formed circuit in resonance with the frequency of a generator of harmonic oscillations, fixing of the own parameters of the sensor at the resonant frequency, placing the sampler with the electrolyte on the operating end face of the eddy current sensor, coaxially thereof, according to the invention, recording the change of the introduced active resistance of the parametric eddy current sensor rated against its own induction resistance while varying the geometry of the eddy current sensor—sampler system, the number of the sensor windings and the frequency of its magnetic field, comparing the adjusted values of the introduced active resistance values, determining the frequency range within which the conductivity of the electrolyte is not dependent on the frequency, calculating the value of the specific electrical conductance.

The frequency characteristic of the sensor's own Q-factor is measured, the first operating frequency is registered that corresponds to the maximum Q of the first frequency at which measurements of the relative active introduced resistance of the sensor with the sample are performed. After measuring at the first operating frequency the sensor's diameter is increased by q times while reducing by q2 times the first operating frequency, thus registering the zero operating frequency at which the introduced resistance of the sensor with the sample is measured.

The values of the active introduced resistance rated against the own reactive resistance of the sensor at the first operating frequency are compared with the similar resistance at the zero operating frequency multiplied by the relations of the own inductances of the sensors at the zero and the first operating frequencies, and by the value 1/q, as well as with the similar resistance at the second operating frequency multiplied by the relation of the own inductances of the sensors at the second and the first operating frequencies and by the value q, also taking into regard the corrections of the incomplete compensation of the clearance at the zero and the second operating frequencies. The value of the specific electrical conductance of the electrolyte is determined according to the value of the relative active introduced resistance at the first operating frequency if the values compared in p. 5 coincide with an accuracy of up to 10%.

The number of turns in the coil of the eddy current sensor is changed if the adjusted values of the relative introduced resistances measured at the zero and second operating frequencies, as well as the value of the introduced resistance at the first operating frequency differ from one another by more than 10%. In such case a new value of the first operating frequency is determined, and the operations of measuring and comparing the introduced resistances are repeated.

The winding wire diameter and the winding pitch are selected to correspond with the maximum sensitivity of measurements while the own resonant frequency of the eddy current sensor that is determined by the values of its inductance and parasitic inter-turn capacitance should be at least by an order higher of the second operating frequency value. The winding wire diameter and the winding pitch are maintained constant for each triple of sensors of different diameters but with an equal number of turns.

Each triple of eddy current sensors having an identical number of turns and operating the zero, first and second frequencies are coaxially joined into an integral structure of the primary pickup transducer, while the sampler with the electrolyte is placed on the operating end face of the transducer with the symmetry center of the sampler base to be coincident with the symmetry axis of the primary transducer. The distance between the nearest to the electrolyte surface turn of each sensor of the first pickup transducer and the electrolyte surface in the sampler is set to be proportional to the sensor radius.

BRIEF DESCRIPTION OF THE DRAWINGS

The essence of the proposed method is illustrated by the figures and graphs shown in FIGS. 1–6.

DETAILED DESCRIPTION OF THE INVENTION

The electrolyte conductivity is measured in a vortex magnetic field using a laid-on eddy current sensor without any contact with the matter being studied, thus such measurements refer to the class of noncontact measurements.

The thin-wall sampler made of a rigid dielectric material with a flat bottom is installed onto a laid-on eddy current sensor. The sensor is made in the form of a short cylindrical induction coil with a number of turns W. The sampler is arranged so that the symmetry center of its base and symmetry axis of the eddy current sensor are approximately coincident. In such case the radial dimensions of the sampler should be at least two times higher of the sensor's diameter D. In this case the minimum distance between the turn on the operating end face of the sensor and the lateral edge of the sample is not less than the sensor's radius. It is anticipated that the inner radial dimensions of the sampler and the sample are approximately coincident.

Figure 1:
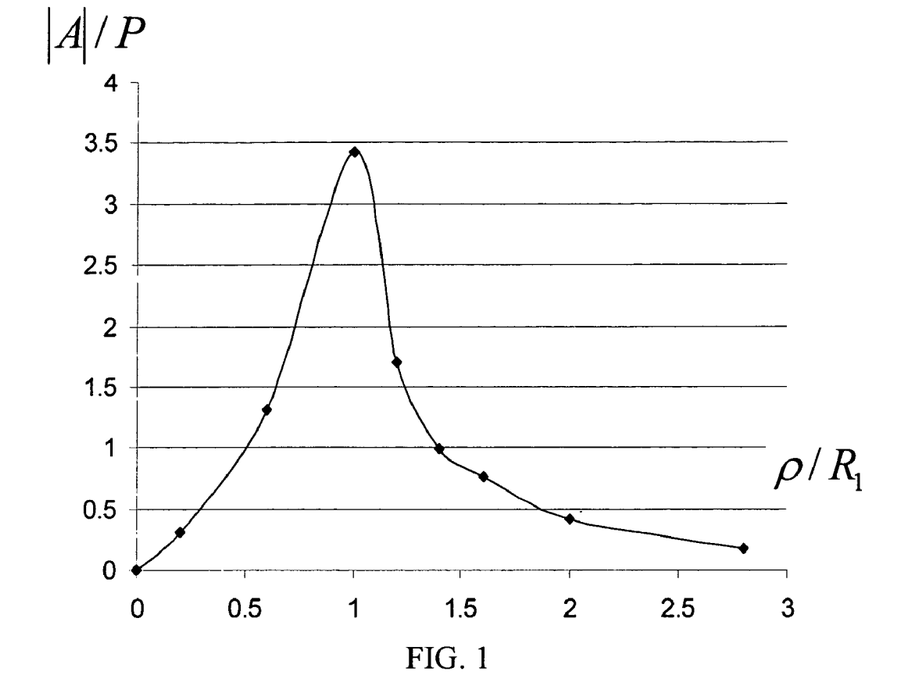
FIG. 1. Relationship between the rated value of the magnetic field vector potential of turn A in the free space and ratio $p/R_1$ at $Z/R_1=0$. Here $R_1$ is the turn radius; p,Z are coordinates of the cylindrical system of coordinates.

Vector-potential of the turn's magnetic field with a harmonically variable current, located in the free space, in case when the center of the cylindrical system of coordinates is found in the turn's center, can be presented as [2]:

$$A = \frac{\mu_0 I R_1}{2} \int_0^\infty J_1(\lambda R_1) J_1(\lambda \rho) e^{-\lambda|z|} d\lambda, \qquad (1)$$

where $I=Ie^{i\omega t}$—current in the turn; $R_1$—turn radius; $\mu_0$—magnet constant; $J_1$—Bessel's function of $1^{st}$ order, λ—conversion parameter; ρ, z—coordinates in the cylindrical system of coordinates. The integral in (1) is expressed through the complete elliptical integrals of the first E and the second K kind, whose tables are contained in a number of mathematical reference books including [3]:

$$A = \frac{\mu_0 I}{\pi \kappa} \sqrt{\frac{R_1}{\rho}} \left[ \left(1 - \frac{\kappa^2}{2}\right) K(\kappa) - E(\kappa) \right], \quad (2)$$

$$\text{where } \kappa^2 = \frac{4 R_1 \rho}{(R_1 + \rho)^2 + z^2}$$

The magnetic field intensity is directed along the coordinate φ and is proportional to the magnetic field vector potential A. The e.m.f. induced by the magnetic field of the turn in any circuit coaxial thereto, and equal to the circulation of vector E in this circuit, is also proportional to the vector potential. Hence, value A is a convenient characteristic of the turn's field. FIG. 1 shows the calculated according to formula (2) dependence of value |A|/p, where $p=\mu_0 I/\pi$=const, on relation $\rho/R_1$ within the turn's plane, that is when z=0. It follows from this graph that the vector potential of the magnetic field A is at its maximum when the distance from the turn's center is $p=R_1$, while at the distance $\rho=2R_1$ its value already reaches 10% of the maximum value (during the calculations it is assumed that at point $p=R_1$ α=arcsin k=89°). In such case if the minimum distance from the turn on the operating end face of the sensor ($p=R_1$) to the lateral edge of the sample, as it was specified above, is not less than the radius of the sensor ($\rho \geq 2R_1$), then the field beyond the sample can be neglected.

Parallel to the eddy current sensor a capacitor is switched whose capacitance can be varied. The parallel oscillating circuit formed in such case is switched to a generator of harmonic oscillations and is tuned in resonance with its frequency.

At the resonant frequency the Q-factor $Q_0$ and capacitance $C_0$ of the non-loaded sensor are measured, that is of the sensor without a sample, whereupon on the sensor a dielectric sampler with the electrolyte is installed while the capacitance of the oscillating circuit is tuned in such a manner that it is again brought to a resonant duty, fixing the resonant values of $Q_1$ and $C_1$. The value of the active resistance $R_V$ introduced into the sensor and rated against the own induction resistance of the sensor $X=\omega L_0$ is determined by formula:

$$\frac{R_v}{\omega L_0} = \frac{Q_0 C_0 - Q_1 C_1}{Q_0 Q_1 C_1} \quad (3)$$

Figure 2:
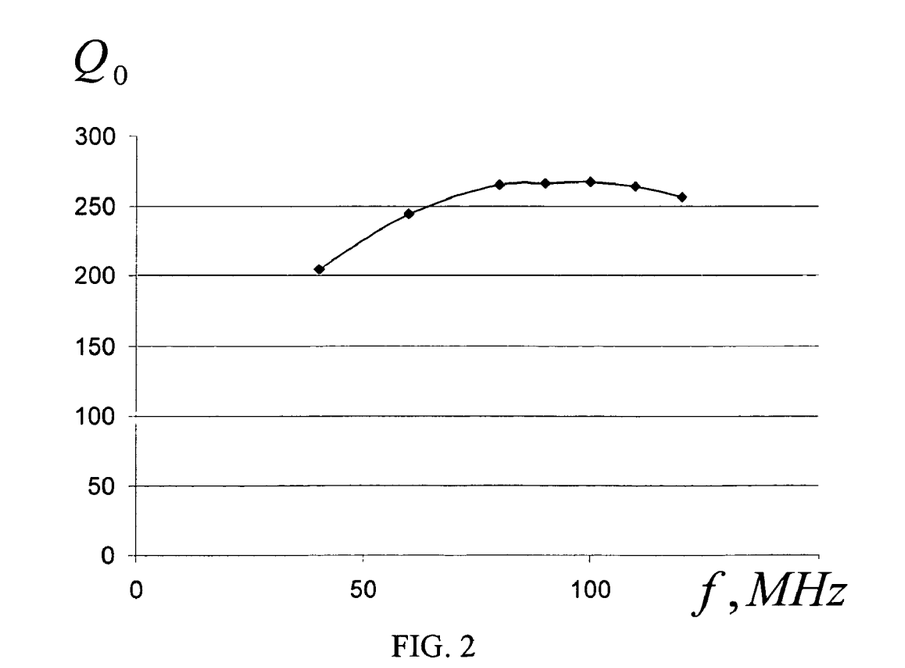
FIG. 2. The experimental frequency characteristic of the own Q-factor of the eddy current sensor.

The own Q-factor of the eddy current sensor, as of any inductance coil, is a function of frequency. The inductance coil Q-factor equals $Q=\omega L_0/r$, where $\omega L_0$ is its inductance resistance, and r—active resistance. With the increasing frequency the inductance resistance and the Q-factor grow. But with the frequency increase the current flowing in the wire (winding) of the coil is more and more transferred to the surface layers of the wire (skin effect), and the active resistance r increases. Starting from a certain frequency an increase of r in the denominator begins to prevail over the increase of $\omega L_0$ in the numerator, and then with the increase of frequency the Q-factor begins to get lower. The frequency corresponding to the Q-factor maximum is determined by recording the frequency characteristic of the own Q-factor of the eddy current sensor. At this frequency the sensor sensitivity is maximum. Therefore it is chosen as the first operating frequency at which the relative introduced active resistance of the sensor with the sample is measured.

The experimental frequency characteristic of the own Q-factor of the eddy current sensor is shown in FIG. 2.

After measuring (at the first operating frequency) the relative active resistance $R_V/\omega L_0$ introduced into the eddy current sensor by the electrolyte sample the sensor diameter is increased by q times. According to the theory of the strap type parametric sensors value $R_V/\omega L_0$ can be expressed in the form:

$$\frac{R_v}{\omega L_0} = \sqrt{2} \pi \mu_0 R_1 W^2 \beta F(\alpha, \beta, \xi), \quad (4)$$

where $R_1$—sensor radius; $\mu_0=4\pi \cdot 10^{-7}$ GN/m—magnetic constant; W—number of sensor turns; $\alpha=2h/R_1$ (h—the distance between the edge turn of the sensor and the electrolyte surface nearest thereto); $\beta=R_1\sqrt{\omega\sigma\mu_0}$ (ω—frequency, σ—specific electrical conductance); $\xi=2d/R_1$ (d—sample thickness of the liquid or solid electrolyte). Function F has a complex nonmonotonous character and is presented in the form of an integral that is not expressed through the known functions. The value of this integral is usually found using digital methods or by means of approximated expressions as a function of parameters α, β, ξ. In such case, to prevent any change of parameter α with the change of the eddy current radius, distance h from the edge turn of the sensor to the nearest surface of the electrolyte is set proportional to the sensor radius.

Any change of value $R_V/\omega L_0$ will be influenced only by the change of value β, since the other parameters of formula (4) are known.

By increasing the sensor radius by q times while simultaneously reducing the first operating frequency by $q^2$ times we shall obtain the same value of the total parameter β (Zennek's parameter).

When comparing $R_{V1}/\omega_1 L_0^{(1)}$, obtained at the first operating frequency, with the value $$\frac{R_{V0}}{\omega_0 L_0^{(0)}} \frac{L_0^{(0)}}{L_0^{(1)}} \frac{1}{q} p(\alpha_0) = \frac{R_{V0}}{\omega_0 L_0^{(1)}} \frac{1}{q} p(\alpha_0), \quad (5)$$

(where $L_0^{(1)}=L_0$, $\rho(\alpha_0)$—correction of the incomplete compensation of the clearance at the zero frequency) obtained at the zero operating frequency their equality is achieved only if the electrical conductance of the electrolyte is not dependent on frequency in the range $\omega_0$–$\omega_1$.

After measurements at the first and the zero operating frequencies the sensor diameter is reduced relative to the initial diameter by q times, with the corresponding frequency increase by $q^2$ times, thus fixing the second operating frequency $\omega_2$, at which the introduced resistance of the sensor with the sample is measured. When comparing $R_{V1}/\omega_1 L_0$, obtained at the first operating frequency, with value $\rho(\alpha_2)qR_{V2}/L_0^{(2)})$ obtained at the second operating frequency they will become equal at the constant electrical conductance within the frequency range $\omega_1$–$\omega_2$.

In such manner a comparison is made of the value $R_{V1}/\omega_1 L_0^{(1)}$ obtained at the first operating frequency with the value $R_{V0}/\omega_0 L_0^{(0)}$ obtained at the zero operating frequency, multiplied by $\rho(\alpha_0)L_0^{(0)}/qL^{(1)}$; as well as with the value $R_{V2}/\omega_2 L_0^{(2)}$, obtained at the second operating frequency and multiplied by $q\rho(\alpha_2)L_0^{(2)}/L_0^{(1)}$. In case of their equality:

$$\frac{R_{v0}}{\omega_0 L_0^{(0)}} \frac{L_0^{(0)}}{L_0^{(1)}} \frac{1}{q}\rho(\alpha_0) = \frac{R_{v1}}{\omega_1 L_0^{(1)}} = \frac{R_{v2}}{\omega_2 L_0^{(2)}} \frac{L_0^{(2)}}{L_0^{(1)}} q\rho(\alpha_2), \quad (6)$$

where $\omega_0$, $\omega_1$, $\omega_2$—correspondingly the zero, first and second operating frequencies; $L_0^{(0)}$, $L_0^{(1)}$, $L_0^{(2)}$—correspondingly the own inductances of the sensors operating at these frequencies; the electrical conductance of the electrolyte does not depend on the frequency within the range from $\omega_0$ to $\omega_2$.

If equation (6) is fulfilled, that is the electrical conductance of the electrolyte is constant and does not depend on frequency in the range from $\omega_0$ to $\omega_2$, then the specific electrical conductance of the electrolyte is determined according to the value of the relative active introduced resistance at the first operating frequency ($\omega_0 < \omega_1 < \omega_2$), at the maximum point of the own Q-factor of the sensor, that is with the maximum sensitivity.

From the practical viewpoint, taking into regard the frequency range in which the eddy current measurements of the electrical conductance of electrolytes are performed, the number of turns and the radial dimensions of the eddy current sensors, in order to maintain a high sensitivity of the measurements we propose to select valueq within the range q=1.3–1.8.

Liquid electrolyte, similar to the solid electrolyte, contains two basic types of charges: free and bound charges. Correspondingly, the electrical conductance of the electrolyte also has two components.

The first of them that is dependent on the movement of the free charge carriers is determined by the formula:

$$\sigma_0 = F\eta\phi(U_+^0 + U_-^0), \quad (7)$$

where F—Faradey's number (F=$qN^1$: q—the charge carried by each ion; $N^1$—the number of molecules in gram-equivalent); $\eta = n_0/N^1$ ($n_0$—number of molecules of the dissolved substance per volume unit); $\phi$—dissociation coefficient; $U_+^0 + U_-^0$—total of movements of the positively and negatively charged ions.

This conductance $\sigma_0$, caused by the directed movement of ions under the action of the electric field is termed as the electrolytic conductance and is often independent (at least up to the decimeter band frequencies. It is the parameter that is to be determined.

The presence of the bound charges is explained by the polarization of the substance. The polar molecules feature a constant dipole moment even in the absence of an electric field. When an outer field is laid over, the molecules strive to turn in such a manner as to be located along the intensity lines. Besides, the dipole is also subjected to the action of a force that is proportional to the dipole moment and field intensity gradient. This force shifts the dipole into the region of the maximum field intensity [1,4]. Since in our case the circuit of the maximum intensity of the electric field is formed directly under the turn of the eddy current sensor, the bound charges will be shifted into that region.

While initially a molecule has no dipole moment (non-polar molecule), under the influence of the outer electric field the charges are shifted therein and a dipole moment appear in it. In case of non-rigid polar molecules the total dipole moment will change for two reasons: due to the increase of dipole moments and due to their shift in the inhomogeneous field.

Taking into regard the presence in the medium both the non-polar molecules (model of Klausis-Mosotti) and the polar molecules (Debay's model) the polarization vector can be presented in the form [4]:

$$P = \alpha n_0 E_1 + n_0 \frac{P_0^2 E_1}{3kT}, \quad (8)$$

where $\alpha$—coefficient of molecule polarization, $n_0$—number of molecules per volume unit, $P_0$—own dipole moment of a molecule, $\kappa$—Bolzman's constant, T—absolute temperature, $E_1$—average intensity value of the electric field acting on the molecules In formula (8) nthe first addend is comprised of a so-called resilient polarization while the second addend—relaxation polarization.

A mathematical description of the relaxation polarization was pioneered by Deby [4,5]. According to his theory the dielectric permeability can be represented in the form $$\varepsilon(j\omega) = \varepsilon'_\infty + \sum_i \frac{\Delta\varepsilon_i}{1 + j\omega\tau_i}, \quad (9)$$

where $\epsilon'_\infty$—the permeability that corresponds to the resilient polarization (at optical frequencies); $\Delta\epsilon = \epsilon_{\omega_0} - \epsilon_\infty$; $\epsilon_{\omega_0}$—quasi-static value of penetrability; $\tau$—relaxation time.

The description $\epsilon(j\omega)$ according to (9) is valid for a discrete distribution of the relaxation times. When the relaxation time is changing continuously a corresponding function is introduced that describes such change, and the sum in (9) is replaced with an integral.

The total current density in the material containing both free and bound charges comprises a sum of the conduction current density and the shift current density. Taking into regard the two components of the polarization vector (9) the expression for the total current density can be presented in the following form $$J = J_{con} + J_{cap} + J_{pol} = \sigma_0 E + j\omega\varepsilon_0\varepsilon'_\infty E + j\omega\varepsilon_0 \sum_i \frac{\Delta\varepsilon_i}{1 + j\omega\tau_i} \quad (10)$$

Here the first addend corresponds to the conductance current density, the second—to the capacitance current density, while the third corresponds to the polarization current density.

As it is seen from (10), the conductance current coincides in its phase with the field intensity while the capacitance current is ahead of the intensity E by 90°. Because of the losses caused by the friction of the particles being polarized the polarizing current is ahead of the field intensity by an angle that is less than 90°, that means that it can be divided into two components that correspondingly coincident in their phase with the conductance current and the capacitance current. In view of this in practical calculations not every separate density component of the three specified density components of the total currents of interest, but the total density of the active and the total density of the reactive components. In such case it is reasonable to introduce a notion of the integral specific conductance and of the integral dielectric penetrability.

By dividing in (10) the real and the imaginary components we obtain:

$$\tilde{\sigma} = \sigma' + j\sigma'' \tag{11}$$

$$= \left[\sigma_0 + \omega\varepsilon_0 \sum_i \frac{\omega\tau_i \Delta\varepsilon_i}{1+(\omega\tau_i)^2}\right] + j\omega\varepsilon_0 \left[\varepsilon'_\infty + \sum_i \frac{\Delta\varepsilon_i}{1+(\omega\tau_i)^2}\right]$$

As follows from (11) the real conductance component $\sigma'$ (hereinafter we shall name it simply conductance) consists of a frequency-independent part $\sigma_0$, caused by the movement of the free charge carriers, and of the frequency-dependent part $\sigma_f$:

$$\sigma' = \sigma = \sigma_0 + \sigma_f \tag{12}$$

In electrolytes $\sigma_0$ is caused by the movement of ions and is determined by the expression (7).

The value of frequency-dependent conductance according to (11) is equal to:

$$\sigma_f = \omega\varepsilon_0 \sum_i \frac{\omega\tau_i \Delta\varepsilon_i}{1+(\omega\tau_i)^2} \tag{13}$$

In this formula the factor of $\omega$ is the coefficient of dielectric losses $\epsilon''$.

Figure 3:
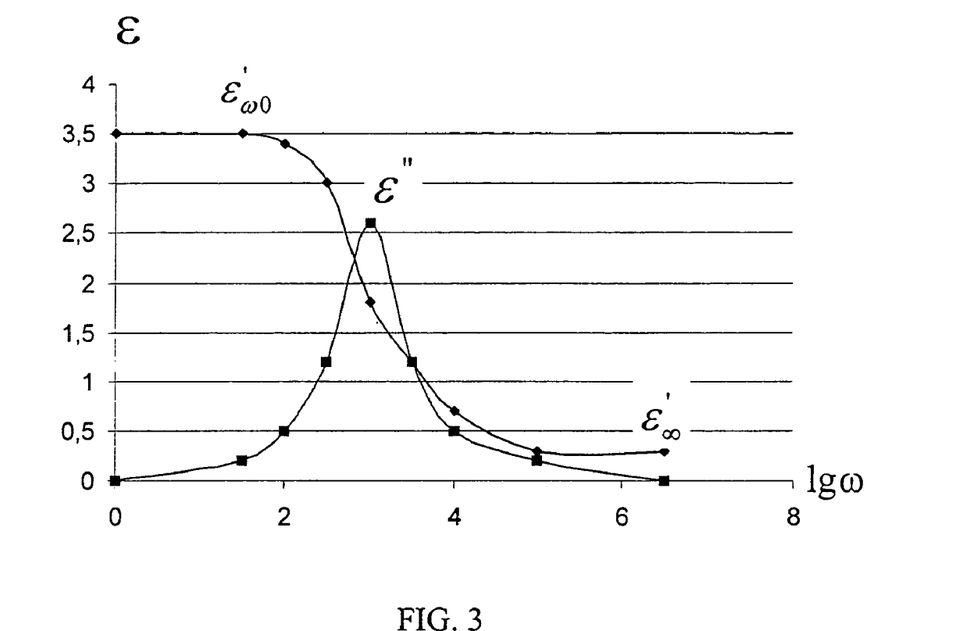
FIG. 3. Relationship between the components of the integral dielectric penetrability and the frequency for the same relaxation time.

It should be noted that one relaxation time T has a relatively limited range of materials. As a typical example here serves ice made of distilled water at substantial negative temperatures. The frequency relationships for such materials have the form shown in FIG. 3. However, for the majority of liquid and solid materials including polymers the dispersive region at frequency relationships turns to be blurred. In polar molecular systems there exists a set or a range of relaxation times that cause expansion of the dispersive region. The character of the distribution function related to the structure of the material can be rather different [5,6].

Thus, the frequency relationship $\sigma_f$ caused by the shift of the bound charges in electrolytes, and transformation of the frequency relationship during an increase of salt concentration in the electrolyte has a complex character which it is practically impossible to determine apriori.

If the results of comparing the adjusted introduced resistances of the eddy current sensors that are measured at the zero, first and second operating frequencies do not coincide, that is if the equation (6) is not within a 10% error limit, it means that the electrolyte electrical conductivity $\sigma'$ (12) contains a component $\sigma_f$ dependent on the frequency that is explained by the fact that the operating frequency range is within the extremum region of the frequency characteristic $\epsilon''$.

If the adjusted values of the relative introduced active resistances measured at the zero and second frequencies, as well as the value of the relative introduced active resistance measured at the first operating frequency differ more than by 10%, the number of turns in the coil of the eddy current sensor is changed whereupon the new value of the first operating frequency is determined and again are repeated the operations for increasing and reducing the diameter of the sensors and for carrying out the respective measurements with their help. These actions result in a shift of the frequency range within which the electrical conductivity is being studied, both into the region of lower and in the region of higher frequencies. In such manner a search of the frequency region is performed beyond the extremum region $\epsilon''$, or where the electrolyte conductivity $\sigma$ is determined only by the component $\sigma_0$ (12) caused by the motion of the free charge carriers.

Taking into regard the length of the conductors that bring the high frequency electric current to the eddy current sensor it is reasonable to limit the minimum number of turns in the sensor to two in order to maintain a high sensitivity of the measurements.

In the process of experiments it was found that the sensitivity of the short cylindrical coil to the active introduced resistance changes with the change of the number of its turns. This sensitivity has its maximum which is observed when the number of turns equals W=3–5, and is a function of the coil diameter, winding wire thickness and distance between the turns in the high frequency range. For maintaining the sensitivity of the measurements it is reasonable that the maximum tolerable number of turns in the eddy current sensor to exceed the value corresponding to the maximum sensitivity not more than twice.

The use of a magnetic-dielectric core, for example, ferritic, in the eddy current sensor coil while operating in the metric wave band is limited by two factors: first, the magnetic permeability of ferrite in the specified frequency band is usually not high, second, it depends on the frequency. Therefore it is reasonable to use a dielectric as the core of the eddy current sensor coil, and to avoid any influence of such a core on the sensitivity of measurements the dielectric loss angle tangent of the dielectric should not exceed $5.10^{-4}$ in the range between the least zero value and the maximum second operating frequency value.

The wire diameter in the sensor coil winding substantially influences its active resistance at all frequencies, including high frequencies at which the current flows in the thin surface layer of the wire. An increase of the own active resistance of the coil reduces the sensor's Q-factor thus reducing the sensitivity of measurements. Therefore the minimum wire diameter is to be not less than one tenth of the coil diameter while the maximum diameter is 1.5 mm when the coil diameters exceed 15 mm.

The own resonant frequency of the eddy current sensor that is determined by the values of its inductance and parasitic inter-turn capacitance should at least by an order exceed the value of the second operating frequency. This means is proposed with the aim to exclude the influence of the own sensor's resonance on the measurement results within the frequency range.

To maintain identical sensitivity and accuracy of measurements at the zero, first and second operating frequencies the wire winding diameter and winding pitch are maintained constant for each triple of the sensors that have different diameters but similar number of turns.

Figure 4:
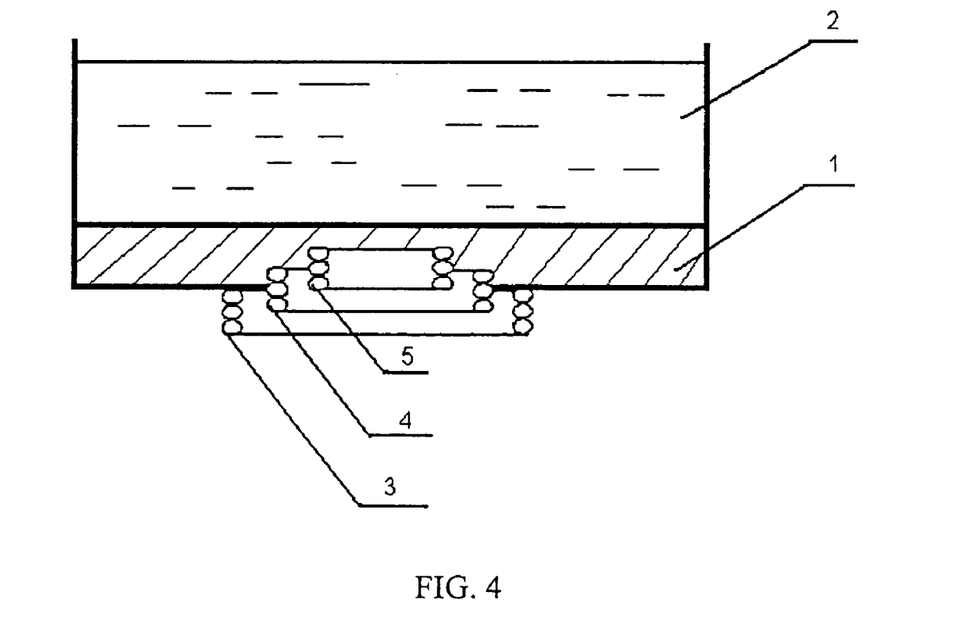
FIG. 4. The primary measuring transducer: 1-dielectric sampler, 2—electrolyte, 3—eddy current sensor of the zero operating frequency, 4-of the first operating frequency, 5-of the second operating frequency FIG. 5. Relationship of the relative active resistance $Rv'=R_v/\omega L_0$ introduced into a short cylindrical coil of the eddy current sensor, and the number of turns W, obtained on samples with electron conductivity—alloyed monocrystals of germanium (coil diameter D=14.7 mm, the specific electrical conductance values σ are indicated on the graphs).

Each triple of eddy current sensors with an identical number of turns that operate at the zero, first and second operating frequencies are unified relative to their common axis into an integral structure of the primary measuring transducer as shown in FIG. 4. The sampler with the electrolyte is placed on the operating end face of the transducer so that the symmetry center of the sampler base should be coincident with the common axis of the primary transducer.

During the operation process, while repeatedly switching the sensors that operate at the zero, first and second operating frequencies, the overall clearance $\alpha=2h/R_1$ (see FIG.

4) should remain constant, at least for the turn that is the nearest to the electrolyte surface whose introduced resistance is the highest in comparison to the other turns of the coil. Otherwise the sensitivity of the measurements for the lower diameter sensor will be much lower than for the higher diameter sensor. Therefore the distance between the nearest to the electrolyte surface turn of each sensor of the primary measuring transducer and the surface of the electrolyte in the sampler is set to be proportional to the sensor radius. But as the sensor coil has more than one turn, it is impossible to fully compensate the influence of the clearance on the measurement results. Therefore the formulas (5,6) contain corrections for the incomplete clearance compensation at the zero and the second operating frequencies. These corrections are calculated according to the values of the overall clearance for each turn of the eddy current sensor coil.

To avoid any reduction of the sensors' Q-factor by the material of the sampler the latter is made of a dielectric whose dielectric loss tangent angle does not exceed $10^{-3}$.

The essence of the invention is illustrated by the non-limiting examples given below.

EXAMPLE 1

The example illustrates the methodology of selecting the first operating frequency.

The relationship between the own Q-factor of the eddy current sensor $Q_0 = \omega L_0/r$ and the frequency has an extremal character. The explanation is that with the increase of the frequency the Q-factor is initially predominantly influenced by the growth of the inductance resistance that is found in the numerator. In this case $Q_0$ is increased. Then starts prevailing the increase of the active resistance of the winding wire due to the current expulsion into the surface layer of the wire that has a higher resistance (skin effect).The extremum value and position depend on the geometry of the eddy current sensor, its dimensions, number of turns, availability and properties of the core, surface condition of the winding wire.

FIG. 2 shows the frequency characteristic of the own Q-factor of the eddy current sensor having the following parameters: sensor turn diameter Dav=14.5 mm, number of turns W=3, copper wire diameter $d_0$=1.5 mm, air core.

According to the given graph the first operating frequency corresponding to the maximum Q-factor equals 100 mHz.

EXAMPLE 2

From the expression for the generalized parameter β (4) ($\beta = R_1 \sqrt{\omega \sigma \mu_0}$, where $R_1$ is the radius of the eddy current sensor, ω—field frequency, σ—specific electrical conductance), that determines at the fixed clearance and sample thickness the introduced impedance of the eddy current sensor, it follows that frequency ω influences the value of the relative introduced active resistance $R_v/\omega L_0 = R_v'$ in the same degree as the squared radius of the sensor. Let us check how this theoretical statement is valid for materials with low σ.

The studies were performed on the test samples whose conductance depends on the movement of free charges, electrons and holes. Alloyed monocrystals of germanium and silicon semiconductors were used as electrical conductance test samples. The ohmic character of the conductance of the monocrystals, rather high homogeneity (electrical conductance variation values of the test samples after selection did not exceed 0.5%), absence of frequency dispersion of the electrical conductance within the range to 1000 MHz, the possibility to produce monocrystals with a high temperature stability within the 0–50° C. prove the perspectiveness of using the germanium and silicon monocrystals as test samples for determining the specific electrical conductance σ.

The study was performed for short cylindrical inductance coils with W=10.5. For two coil diameters, for example, $D_1$=10.6 mm and $D_2$=6.8 mm frequencies f =ω/2π were set in such a way that the product $D_i^2 f_i$ remains constant for each coil—$D_i^2 f_i$=(10.6 mm)$^2 \cdot$10 MHz=(6.8)$^2 \cdot$24.3 MHz=1124 m$^2$/s. For each product $D_1^2 f_1$ and $D_2^2 f_2$ the value of the relative introduced active resistance was measured while the monocrystal of the semiconductor was placed with its flat surface directly on the operating end face of the eddy current sensor coil (with a zero clearance), while fixing the values $R'_{v1}$ and $R'_{v2}$. Error ζ was determined as the relation of difference $R'_{v1}$ and $R'_{v2}$ to their average value $\zeta = 2(R'_{v1} - R'_{v2})/(R'_{v1} + R'_{v2})$. For each of the 6 used test samples error ζ was determined at 11 values of the product $D_i^2 f_i$ (i=1 ... 11). We failed to disclose any trend in the relationships between $\zeta_i$ and $D_i^2 f_i$ for each sample in the range from 360 m$^2$/s to 4000 m$^2$/s, therefore ζ was averaged according to 11 values for each test sample. The obtained results are listed in Table 1.

TABLE 1

| σ, Cm/m | $\sigma_1$ = 1,2 | $\sigma_1$ = 17,9 | $\sigma_2$ = 200 | $\sigma_3$ = 1000 | $\sigma_4$ = 20000 | $\sigma_5$ = 50000 |
|---|---|---|---|---|---|---|
| ζ, % | 3,3 | 6,3 | 5,8 | 11,4 | 13,6 | 14,5 |

The conductance range $\sigma_{of}$ the test samples presented in Table 1 at control frequencies f from 7.8 to 280 MHz and sensor diameters from 3.5 to 14.7 mm includes both the case of a quasistationary field in the material and the transition to a wave field. Thus, for example. The wave length λ in ther sample with σ=1000 cm/m calculated using the formula for a flat wave at f=200 MHz is λ=7 mm, that is this value is comparable to the sensor diameter. Therefore the error jump (ζ=11.4 percent and more) occurs with the change of the electromagnetic field character in the medium, that is during the transition from the quasistationary to the wave field.

The values of the specific electrical conductance of the majority of electrolytes used in chemical power sources fit within the range to 200 Cm/m, and for them the electromagnetic field has a quasistationary character and the error of replacing the sensor diameter increase (that is of expanding the eddy current circuit in the sample) by the frequency reduction is not significant.

EXAMPLE 3

This is an example of studying the influence of reducing the number of turns on the introduced resistances $R_{v1}/\omega_1 L_0$ and $R_{v2}/q\omega_2 L_0$.

Figure 5:
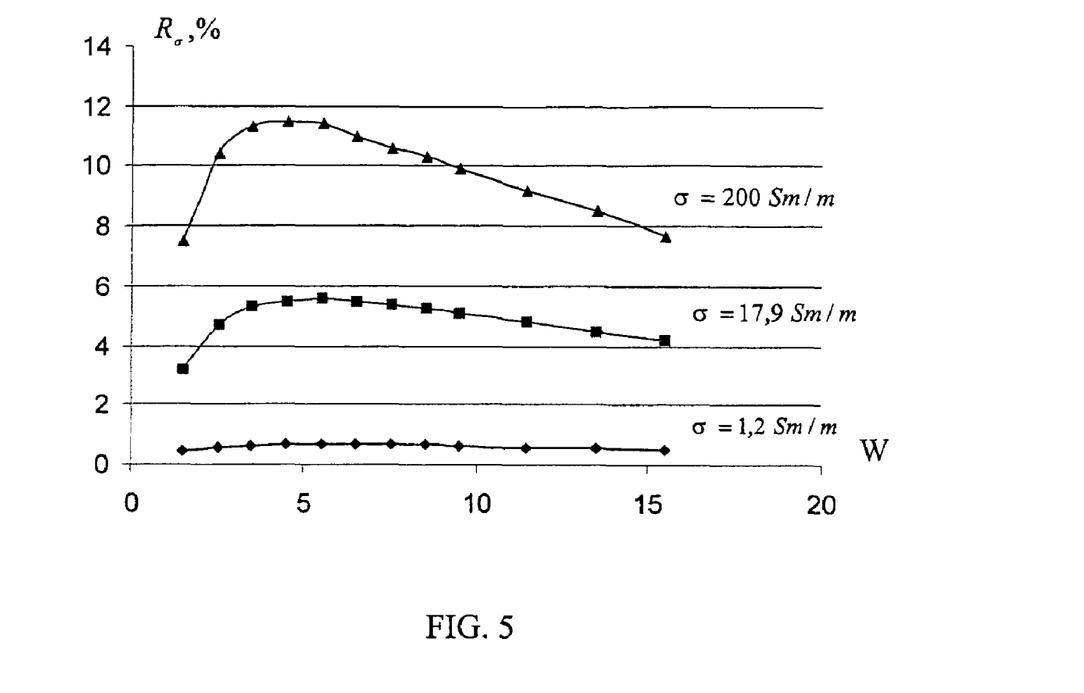

Let us study the changes of the relative introduced active resistance of an eddy current sensor in the form of a short cylindrical inductance coil that occur with the reduction of the number of turns W. FIG. 5 shows the relationships between the relative introduced active resistance $R_v/\omega L_0 = R_v$ of the cylindrically shaped eddy current transducer of diameter D=14.7 mm and the number of turns W closely wound with a 0.4 mm diameter wire, the sensor's magnetic field frequency is f=19.5 MHz. The relationships were obtained on the germanium and silicon monocrystal samples with conductance values σ=1.2; 17.9; 200; Cm/m. An interesting feature of these characteristics is the presence of the maximum. This maximum with the increase of the total parameter $\beta=R_1\sqrt{\omega\sigma\mu_0}$ becomes more vividly expressed and shifts to the field of lower values W.

With the increase of the number of turns from W=1.5 to the number that corresponds to the maximum of the introduced resistance W=W$_{max}$ the absolute value of the resistance R$_\upsilon$ being introduced grows faster than the own inductance L$_0$ of the eddy current sensor. Further, at W>W$_m$ due to the distance increase between the added coil turns and the sample surface their link with the sample gets weaker, the growth rate R$_\upsilon$ decreases while value L$_0$ continues its growth approximately in proportion to W$^2$, thus causing total fall of R$_\upsilon$/$\omega$L$_0$.

Thus, by changing the number of turns it is possible to determine the value of W, that corresponds to the maximum sensitivity of the eddy current sensor to a change in electrical conductance. Hence, the measurements of the $\sigma$ values with such a sensor will be the most accurate.

EXAMPLE 4

This example shows the results of measuring the specific electrical conductance of liquid and solid electrolyte samples using the eddy current method.

The studies were performed on samples of liquid electrolytes Пк+LiClO$_4$ with different salt concentration C=0.1M; 0.25M; 0.5M; 0.75M; 1.0 M; 1.5M.

In the final variant, after varying the diameter and number of turns the sensor that was used to determine the electrical conductance comprised of a short cylindrical inductance coil of diameter D=14.5 mm and number of turns W=3, the winding copper wire diameter d$_0$=1.5 mm. Operating frequency band: 40–120 MHz. Tesla BM-409G Q-factor meter was used during the studies.

To determine the specific electrical conductance $\sigma$ of the electrolytes we shall use an approximated expression [2,7]

$$Z_\upsilon = 48 \cdot 10^{-7} \omega R_1 W^2 e^{-\frac{3}{2}\alpha} \beta^2 \frac{th\frac{3}{4}\xi\sqrt{9+j4\beta}}{3\sqrt{9+j4\beta^2}+(9+j2\beta^2)th\frac{3}{4}\xi\sqrt{9+j4\beta^2}}, \quad (14)$$

where Z$_\upsilon$—the integral resistance introduced into the eddy current sensor; $\omega$—angular frequency; R$_1$—eddy current sensor coil radius; W—number of coil turns; $\alpha$=2h/R$_1$, where h—the distance between the coil turn that is the nearest to the surface of the sample being studied and the electrolyte surface; $\beta=R_1\sqrt{\omega\sigma\mu_0}$, where $\sigma$—electrolyte specific electrical conductance, $\mu_0$—magnetic penetrability in vacuum ($\mu_0$=4$\pi$·10$^7$ GN/m), th—hyperbolic tangent; $\xi$=2d/R$_1$, where d—electrolyte layer thickness.

For each of the three turns of the eddy current sensor coil the distance to the material surface is different: h$_1$=1.5 mm; h$_2$=h$_1$+d$_0$=3 mm; h$_3$=h$_2$+d$_0$=4.5 mm, where d$_0$=1.5 mm—coil wire diameter. In such case $$\left(e^{-\frac{3}{2}\alpha}\right)_{cp} = 0{,}33 \quad (15)$$

Figure 6:
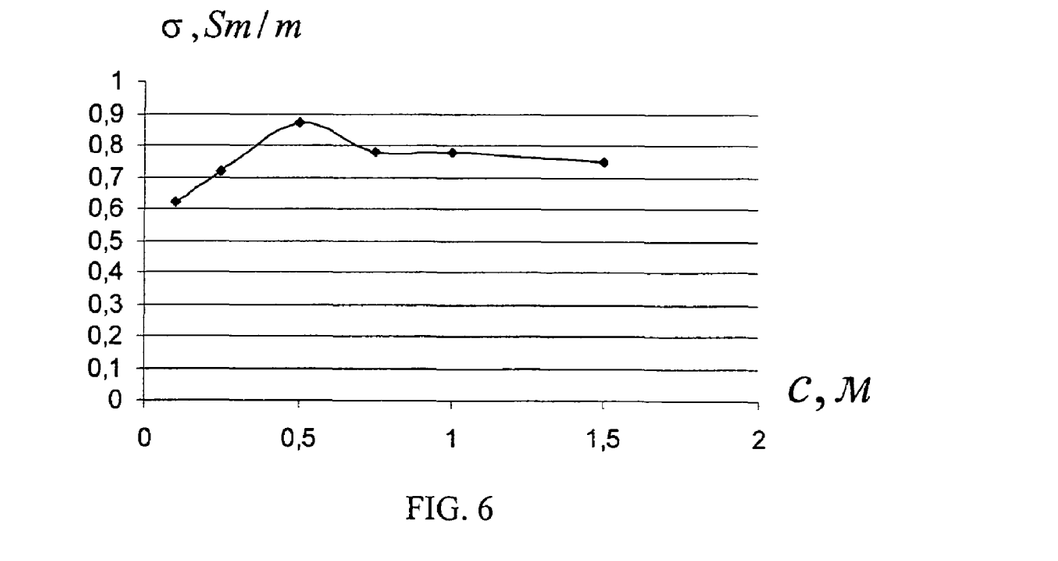
FIG. 6. Relationship between the specific electrical conductance σ of the liquid electrolyte ПК+LiClO$_4$ and the salt concentration.

From (14) using (15) and the data fixed in the experiment it is possible to determine the values $\sigma$. The relationship between $\sigma$ and LiClO$_4$ salt concentration in the electrolyte measured at 60 MHz frequency is shown in FIG. 6.

An increase of $\sigma$ with the increase of concentration C observed in the minor concentration range is explained by the growth in the number of molecules per unit volume of the electrolyte. After the maximum range the determining factor is the reduction of the specific electrical conductance at substantial salt concentrations. The obtained data correspond with the results obtained by other researchers when using the alternating current contact methods.

Similar noncontact studies were carried out for the liquid electrolyte Пк+LiCF3SO3.

The operating frequency range was determined: 30–90 MHz. The obtained relationship between the specific electrical conductance and concentration is shown in Table 2.

TABLE 2

| | Salt concentration, M | | | | | | |
|---|---|---|---|---|---|---|---|
| | 0,1 | 0,25 | 0,5 | 0,75 | 1,0 | 1,5 | 1,75 |
| $\sigma$, Cm/m | 0,20 | 0,24 | 0,28 | 0,31 | 0,32 | 0,32 | 0,30 |

For comparison the contact measurements of electrical conductance of the same electrolyte were performed in a glass dish using platinum electrodes with alternating current. The specific conductance values arfe approximately, with a maximum error of the order of 30% coincide with those listed in Table 2. A rather long transition process was observed during the measurements in the dish. Table 3 shows the parameters of this transition process. Here $\sigma_s$ is the stabilized value of electrical conductance in percentage relative to the initial the electrical conductance was reduced with time), t is the time from the start of the transition process.

During the noncontact eddy current conductance measurements of this electrolyte there were no transition processes. Hence, the eddy current measurements substantially exceed the required rate of measurements which is of high importance during numerous measurements in industrial conditions.

The noncontact eddy current measurements according to the proposed invention were carried out for samples of solid electrolytes Li$_2$O—Li$_2$SO$_4$—B$_2$O$_5$ (50-20-30).

TABLE 3

| Concentration, M | $\sigma$s, % | t, min |
|---|---|---|
| 0.1 | 98.36 | 13.5 |
| 0.25 | 97.3 | 12.5 |
| 0.5 | 92.22 | 15.5 |
| 0.75 | 92.4 | 14 |
| 1.0 | 87.8 | 15 |
| 1.5 | 77.4 | 17 |
| 1.75 | 81.2 | 16 |

In total 10 samples were studied that had various thickness in the range between 0.7–1.15 mm. An operating frequency range of 120–200 MHz was established. The results of measuring the specific electrical conductance are listed in Table 4.

TABLE 4

| | Sample thickness, mm | | | | | | | | | |
|---|---|---|---|---|---|---|---|---|---|---|
| | 0,9 | 1,0 | 0,85 | 0,95 | 0,7 | 0,75 | 0,95 | 1,15 | 1,1 | 0,9 |
| σ, Cm/m | 0,34 | 0,36 | 0,38 | 0,35 | 0,40 | 0,38 | 0,35 | 0,34 | 0,40 | 0,39 |

The result of contact measurements using an indium-gallium amalgam rubbed into the sample gave lower values of the specific electrical conductance that are found within the range of 0.18–0.31 Cm/m. In such case it should be noted that the process of rubbing the amalgam into the opposite faces of a sample of the solid electrolyte is rather lengthy, and after rubbing in and measuring the electrical conductance the sample cannot be used as an electrolyte as it is impossible to remove the amalgam diffused into the depth of the electrolyte.

The proposed method and the primary measuring transducer can be operated when measurements are performed in an automatic mode. This also allows using the proposed invention for noncontact measuring the conductivity of various flowing liquids, for example in a pipeline.

REFERENCES CITED

U.S. Pat. No. 2,542,057, Feb. 20, 1951, Relis, G01N 027/02
U.S. Pat. No. 3,806,798, Apr. 23, 1974, Gross, G01N 027/07
U.S. Pat. No. 4,220,920, Sep. 2, 1980, Gross, G01N 027/07
U.S. Pat. No. 4,408,202, Oct. 4, 1983, Fales, G09G 003/16
U.S. Pat. No. 4,820,990, Apr. 11, 1989, Moore, G01R 005/28
U.S. Pat. No. 4,825,168, Apr. 25, 1989, Ogava et. al, G01N 027/06
U.S. Pat. No. 5,077,525, Dec. 31, 1991, West et al, G01N 027/02
U.S. Pat. No. 5,517,332, Oct. 20, 1992, Reese et al, G01 N 027/02
FR 2782802 A1, Mar. 03, 2000, Coudray Pascal et al., G01 N 027/06
1. Hladic J. Physics of electrolytes. Vol.1, Academic Press, 1972, 555p.
2. Grinberg G. A. Selected problems of the mathematical theory of electric and magnetic phenomena. U.S. Pat. No. USSR Academy of Sciences Publishers, 1948, 727p.
3. Wheelon A. D. Tables of summable series and integrals involving Bessel functions. San Francisco: Holden-Day Inc, 1968.
4. William Fuller Brown, J R. Dielectrics. Spinder-Verlag, Berlin, 1956, 311 p.
5. Frohlich H. Theory of dielectrics—dielectric constant and dielectric loss. Oxford, Clarendon Press, 1949, 180 p.
6. Havriliak S., Negami S. A complex plane representation of dielectric and mechanical relaxation process in some polymer, 1967, vol. 8, No4, p.161–310.
7. Strap and screen type sensors. Novosibirsk, "Nauka" Publishers, 1967, 149 p.

We claim:

1. A method of noncontact measuring the electric conductivity of electrolytes by means of a primary measuring transducer comprises the steps of: placing the electrolyte in a sampler, exciting an alternating magnetic field while using an axisymmetrical eddy current sensor, switching a capacitor of variable capacitance to the sensor, tuning of the formed circuit in resonance with the frequency of the generator of harmonic oscillations, fixing the own sensor parameters at the resonant frequency, placing the sampler with the electrolyte on the operating end face of the eddy current sensor co-axially thereof, calculating the components of the introduced sensor impedance, wherein a change is recorded of the introduced active resistance of the parametric eddy current sensor rated relative to its own inductance resistance while varying the geometry of the eddy current sensor—sampler system, the number of sensor turns and the frequency of its magnetic field by comparing the corrected values of the introduced active the range of frequencies is determined at which the electrolyte conductance does not depend on the frequency, while calculating the value of the specific electrical conductance.

2. A method according to claim 1, wherein is performed measuring of the frequency characteristic of the Q-factor of the sensor, fixing of the first operating frequency that corresponds to the maximum of the Q-factor, at which measuring is carried out of the relative active introduced resistance of the sensor with the sample.

3. A method according to claim 1, wherein after measuring at the first operating frequency the sensor diameter is increased by q times while reducing by $q^2$ times the first operating frequency, fixing in this manner the zero operating frequency at which measuring is performed of the introduced resistance of the sensor with the sample.

4. A method according to claim 1, wherein after measuring at the first and zero operating frequencies the sensor diameter is reduced relative to the initial diameter by q times while increasing by $q^2$ times the first operating frequency, fixing in this manner the second operating frequency at which measuring is performed of the introduced resistance of the sensor with the sample.

5. A method according to claim 1, wherein the values are compared of the active introduced resistance rated relative to the sensor own reactive resistance at the first operating frequency with the similar resistance at the zero operating frequency multiplied by the relations of the own inductance values of the sensors at the zero and the operating frequencies and by the value 1/q, as well as with the similar resistance at the second operating frequency multiplied by the relation of the own inductance values of the sensors at the second and the first operating frequencies and by the value q, also taking into regard the corrections of the incomplete compensation of the clearance at the zero and second operating frequencies.

6. A method according to claim 1, wherein the value of the electrolyte specific electrical conductance is determined according to the value of the relative active introduced resistance at the first operating frequency if the values that were compared in p. 5 coincide with an accuracy to 10%.

7. A method according to claim 1, wherein the value of q is selected within the 1.3–1.8 range.

8. A method according to claim 1, wherein the number of turns in the eddy current sensor coil is changed if the corrected values of the relative introduced resistance values measured at the zero and the second operating frequencies, and also the value of the introduced resistance at the first operating frequency differ from each other more than by 10%, whereupon the new value of the first operating frequency is then determined.

9. A method according to claim 1, wherein the minimum number of turns in the eddy current sensor are set to be equal to two.

10. A method according to claim 1, wherein the maximum number of turns in the eddy current sensor is selected so that it exceeds by two times the value corresponding to the maximum sensitivity of the sensor with a dielectric core.

11. A method according to claim 1, wherein as the material for the core of the sensor coil is selected a dielectric with a dielectric loss tangent angle not exceeding $5.10^{-4}$ within the range from the least value of the zero till the maximum value of the second operating frequency.

12. A method according to claim 1, wherein the minimum wire diameter of the sensor winding coil is set not less than one tenth of the coil diameter, while the maximum diameter is not more than 1.5 mm.

13. A method according to claim 1, wherein the coil wire diameter and the winding pitch are selected to correspond to the maximum sensitivity of measurements while the own resonant frequency of the eddy current sensor that is determined by the values of its inductance and parasitic inter-turn capacitance should be not less than by an order higher of the value of the second operating frequency.

14. A method according to claim 1, wherein each triple of the eddy frequency sensors with an equal number of turns that operate at the zero, first and second operating frequencies are integrated relative to a common axis into a single structure of the primary measuring transducer while the sampler with the electrolyte is placed on the operating end face of the transducer with the symmetry center of the sampler base is to be coincident with the symmetry axis of the primary transducer.

15. A method according to claim 1, wherein the coil wire diameter and the winding pitch are maintained constant for each triple of sensors of different diameters but with an equal number of turns.

16. A method according to claim 1, wherein the distance between the nearest to the electrolyte surface turn of each sensor of the primary measuring transducer and the electrolyte surface in the sampler are set proportional to the sensor radius.

17. A method according to claim 1, wherein during calculations the self-induction coefficients between all paired combinations of turns of the corresponding eddy current sensor are taken into consideration when calculating the value of the specific electric conductance of the electrolyte at the first operating frequency.

18. A method according to claim 1, wherein the sampler is produced of a dielectric material whose dielectric losses tangent angle does not exceed $10^{-3}$.

19. A method according to claim 1, wherein the minimum radial dimensions of the electrolyte sample in the sampler should be not less than two times higher of the maximum diameter of the eddy current sensor from the triple of sensors of the primary measuring transducer.

* * * * *